US00PP24666P3

(12) United States Plant Patent
Schlecht

(10) Patent No.: US PP24,666 P3
(45) Date of Patent: Jul. 22, 2014

(54) ***CHAMAECYPARIS* PLANT NAMED 'CONSCHLECHT'**

(50) Latin Name: *Chamaecyparis obtusa*
Varietal Denomination: Conschlecht

(75) Inventor: Robert J. Schlecht, Center Moriches, NY (US)

(73) Assignee: CP Delaware, Inc., Wilmington, DE (US)

( * ) Notice: Subject to any disclaimer, the term of this patent is extended or adjusted under 35 U.S.C. 154(b) by 285 days.

(21) Appl. No.: 13/385,430

(22) Filed: Feb. 21, 2012

(65) Prior Publication Data

US 2013/0219572 P1 Aug. 22, 2013

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — Kent L Bell
(74) *Attorney, Agent, or Firm* — Buchanan, Ingersoll & Rooney, PC

(57) ABSTRACT

A new and distinct *Chamaecyparis obtusa* plant of unknown parentage is provided that was discovered as a chance seedling while growing in a cultivated area. The new variety readily can be distinguished from other plants of the species in view of its dense compact and rounded growth habit which displays attractive green foliage that is yellow to golden in coloration at the tips when grown in full sun. The plant well resists sun and winter burning and displays good winter hardiness. The plant is well suited for consistently providing attractive ornamentation in the landscape.

1 Drawing Sheet

Botanical/commercial classification: *Chamaecyparis obtusa*/Japanese Cypress Plant.

Varietal denomination: cv. Conschlecht.

SUMMARY OF THE INVENTION

The new Japanese Cypress plant of the present invention is a newly found seedling that was discovered in a cultivated area at the residence of the originator at Center Moriches, N.Y., U.S.A. Other plants of *Chamaecyparis obtusa* (non-patented in the United States) were growing in the area. The exact parentage of the seedling is unknown. The originator was attracted to a single unique seedling primarily in view of its distinctive foliage coloration. The plant was preserved and has been carefully evaluated. Had this single plant of the present invention not been discovered and preserved it would have been lost to mankind.

It has been confirmed that the characteristics of the new plant are reliably expressed.

It has been found that the new *Chamaecyparis* plant of the present invention displays the following combination of characteristics:

(a) displays a dense compact and rounded growth habit,
(b) forms attractive green foliage that is yellow to golden in coloration at the tips when grown under full sun,
(c) resists sun and winter burning,
(d) displays good winter hardiness, and
(e) is well suited for providing attractive ornamentation in the landscape.

At first glance when the new plant is grown in full sun the foliage appears to be yellow to golden in coloration. However, as the branches are separated and more fully observed, yellow-green coloration is apparent below the tips. It has been found that when grown in shaded settings the branches are more consistently green in coloration.

The new plant of the present invention can be grown to advantage to provide attractive ornamentation in the landscape. It can be used as a slow growing foundation planting and/or as a screen planting upon fuller maturity. Attractive colorful ornamentation is made possible over an extended period of time.

The new plant can be readily distinguished from common *Chamaecyparis obtusa* plants (non-patented in the United States) known to inventor in view of its distinctive yellow to golden coloration of the foliage tips when grown in full sun during the growing season and its more rounded growth habit. The foliage of common *Chamaecyparis obtusa* plants tends to be consistently green under the same full sun growing conditions and to be more upright in its presentation.

The new plant also can be readily distinguished to the 'Grippsii' variety of *Chamaecyparis obtusa* (non-patented in the United States) which displays a dwarf more pyramidal open growth habit with consistently bright golden green foliage in full sun when young which turns to bronze in coloration during the winter.

Asexual reproduction of the new plant beginning in 2006 at West Grove, Pa., U.S.A., through the use of semi-hardwood cuttings has demonstrated that the distinctive characteristics are reliably transmitted from one generation to another. Accordingly, the new plant can be asexually reproduced in a true-to-type manner.

The new plant has been named 'Conschlecht' and will be marketed under the NIGHT LIGHT trademark

BRIEF DESCRIPTION OF PHOTOGRAPH

The accompanying photograph shows as nearly true as it is reasonably possible to make the same in a color illustration of this character, a typical specimen of the new variety. A plant at an age of approximately two years is shown while growing in the ground outdoors at West Grove, Pa., U.S.A. The plant had been asexually reproduced through the use of semi-hardwood cuttings and was growing in full sun. The photograph was obtained during November 2008.

DETAILED BOTANICAL DESCRIPTION

The following is a detailed description of the new plant of the present invention which generally was prepared while observing three-year-old plants growing in the ground outdoors during November 2008 at West Grove, Pa., U.S.A. Color terminology is in accordance with The R.H.S. Colour Chart (1995 or equivalent) of The Royal Horticultural Society, London, England, except when general color terms which are to be accorded their customary dictionary significance are used. The growing conditions approximated those employed for the commercial growing of *Chamaecyparis obtusa* plants.

Type: Hardy perennial evergreen for garden decoration and general landscape usage.

Plant:

*Growth habit*.—Slow growing, dense compact, and generally rounded at the top.

*Height*.—Approximately 50 cm at three years of age, and is estimated to be approximately 15 meters at full maturity.

*Width*.—Approximately 50 cm at three years of age, and is estimated to be approximately 3 to 6 meters at full maturity.

*Branching*.—Multiple generally upright main stems commonly arise from the base, secondary stems emerge from main stems, and small sprays emerge from secondary stems in profusion and generally grow upwards.

*Branching habit*.—Freely branching with the branches being primarily erect, branchlets are borne in substantially the same plane and commonly are loosely pendulous towards the apices with the branches and foliage commonly persisting to the soil level.

*Branch length*.—Commonly approximately 10 to 12.5 cm on average.

*Branch texture*.—Somewhat rough.

*Branch color*.—Greyed-Orange Group 166B.

*Spray length*.—Commonly approximately 5 cm.

*Spray width*.—Commonly approximately 2 cm on average.

*Spray color*.—Upper sprays commonly are near Yellow Group 12A and lower sprays commonly are near Yellow-Green Group 144A.

*Branchlet length*.—Commonly approximately 14 cm on average.

*Branchlet diameter*.—Commonly approximately 3 mm.

*Branchlet texture*.—Generally smooth.

*Branchlet color*.—Greyed-Orange Group 164B.

*Internode length*.—On main stems commonly approximately 1 cm on average, and on secondary stems commonly approximately 2 cm on average.

*Roots*.—Dense and freely branching.

Foliage:

*Arrangement*.—Alternate, simple, needle-like and densely imbricate. Fragrance: typical boxwood scent.

*Length*.—Approximately 3 mm on average.

*Width*.—Approximately 3 mm on average at the widest point.

*Apex*.—Acute.

*Base*.—Cordate.

*Venation*.—Not apparent during observations to date.

*Margin*.—Entire.

*Texture*.—On upper and lower surfaces glabrous and slightly glaucous.

*Color*.—When exposed to full sun at the tip commonly measuring approximately ¼ of the branch length commonly is near Yellow Group 4A, and the lower approximately ¾ of the branch not exposed to the sun commonly is near Yellow-Green Group 144A.

*Fragrance*.—Somewhat acrid when crushed.

Inflorescence:

*Flowers*.—None observed during observations to date.

*Fruit*.—None observed during observations to date.

Development:

*Tolerance to diseases*.—No particular disease susceptibility has been encountered during observations to date.

*Resistance to pests*.—No particular susceptibility to pests has been encountered during observations to date.

*Tolerance to heat*.—Has withstood a temperature of 100° F. in absence of sun burning at West Grove, Pa., U.S.A.

*Tolerance to cold*.—Has withstood a temperature of 0° F. in the absence of winter burning at West Grove, Pa., U.S.A.

Plants of the new 'Conschlecht' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Chamaecyparis obtusa* plant having the following combination of characteristics:

(a) displays a dense compact and rounded growth habit, (b) forms attractive green foliage that is yellow to golden in coloration at the tips when grown in full sun, (c) resists sun and winter burning, (d) displays good winter hardiness, and (e) is well suited for providing attractive ornamentation in the landscape;

substantially as illustrated and described.

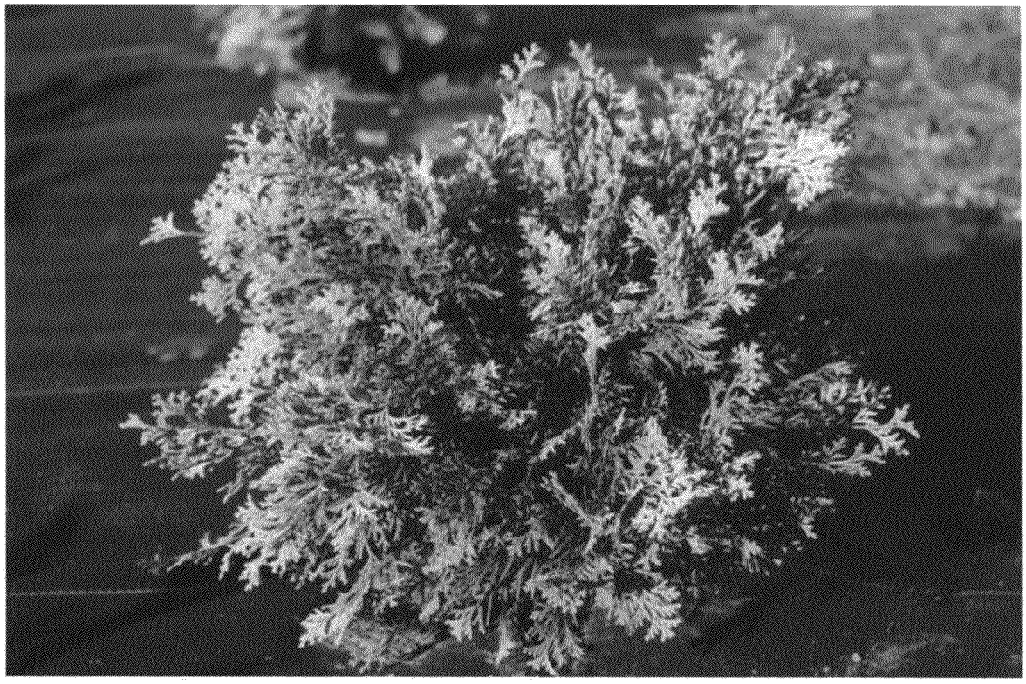

* * * * *